United States Patent [19]
Campbell, Jr.

[11] Patent Number: 5,690,242
[45] Date of Patent: Nov. 25, 1997

[54] SHARPS DISPOSAL CONTAINER CAP SECUREMENT ARRANGEMENT

[75] Inventor: Vance D. Campbell, Jr., San Diego, Calif.

[73] Assignee: Winfield Industries, San Diego, Calif.

[21] Appl. No.: 622,559

[22] Filed: Mar. 25, 1996

[51] Int. Cl.⁶ .................................................. B65D 45/00
[52] U.S. Cl. .......................... 215/273; 215/274; 215/330; 215/901; 215/14; 220/319; 220/379; 206/365; 206/366
[58] Field of Search .................................. 215/263, 273, 215/274, 276, 330, 901, 14, 228; 220/319, 379; 206/364, 365, 366

[56] References Cited

U.S. PATENT DOCUMENTS

| | | |
|---|---|---|
| 3,811,589 | 5/1974 | Thornton et al. ............... 215/276 X |
| 3,905,509 | 9/1975 | Markowitz . |
| 3,924,769 | 12/1975 | Fillmore ............................ 215/216 |
| 3,971,488 | 7/1976 | McRoskey et al. . |
| 3,977,557 | 8/1976 | Hazard . |
| 4,466,538 | 8/1984 | Gianni . |
| 4,494,652 | 1/1985 | Nelson et al. . |
| 4,520,926 | 6/1985 | Nelson . |
| 4,779,728 | 10/1988 | Hanifl et al. . |
| 4,830,207 | 5/1989 | Battegazzore . |
| 4,934,547 | 6/1990 | Mayes et al. ..................... 215/306 |
| 4,936,445 | 6/1990 | Grabenkort . |
| 5,007,546 | 4/1991 | Rose et al. . |
| 5,046,613 | 9/1991 | Baudry et al. . |
| 5,107,990 | 4/1992 | Wicherski et al. . |
| 5,145,063 | 9/1992 | Lee . |
| 5,167,193 | 12/1992 | Withers et al. . |
| 5,178,308 | 1/1993 | Endre . |
| 5,203,838 | 4/1993 | Schneider . |
| 5,224,615 | 7/1993 | Hickerson ........................ 215/218 |
| 5,249,680 | 10/1993 | Shillington . |
| 5,277,312 | 1/1994 | Vumbaca . |
| 5,314,085 | 5/1994 | Collado Bonet . |
| 5,328,046 | 7/1994 | Kutz et al. . |
| 5,360,127 | 11/1994 | Barriac et al. . |
| 5,611,429 | 3/1997 | Phillips .......................... 206/365 |

*Primary Examiner*—Stephen Cronin
*Attorney, Agent, or Firm*—Flanagan & Flanagan

[57] ABSTRACT

A sharps disposal container cap securement arrangement includes a container with a neck having an opening at a top thereof through which sharps may be placed for disposal within the container, a cap adapted to screw downward over and around the neck of the container to close the opening and to provide a fluid-tight seal therewith once the cap is screwed down on the neck, an annular lock collar rotatably mounted around an exterior surface of the neck of the container, detents formed on the exterior surface of the neck of the container and on the collar for supporting the collar on the neck for movement between a lowered unlocked condition and a raised locked condition in response to the lock collar being rotated between first and second positions relative to the neck, and cooperative series of one-way teeth formed on the collar and on the cap for securing the cap to the collar and thereby preventing unscrewing of the cap from the neck of the container once the cap is screwed down on the neck providing the fluid-tight seal and the lock collar has been rotated from the first to second position.

30 Claims, 5 Drawing Sheets

SHARPS DISPOSAL CONTAINER CAP SECUREMENT ARRANGEMENT

BACKGROUND OF THE INVENTION

1. Field of the Invention

The present invention generally relates to disposal containers for materials such as contaminated liquids and sharp instruments and, more particularly, is concerned with a cap securement arrangement for a sharps disposal container.

2. Description of the Prior Art

Many different types of containers exist for storage and disposal of many different types of materials. One special class of containers are those designed specifically for disposal of "sharps," a term widely used to refer to hypodermic needles, razor blades, scalpels and many other sharp instruments. Through use sharps may become contaminated by body fluids and the like creating a hazard for anyone that intentionally or inadvertently handles them following their use. Because of their potentially dangerous nature, used sharps should be disposed within a rigid container having a closure device which inhibits or prevents the intentional or inadvertent handling of the used sharps.

Numerous sharps disposal container designs exist which employ closure devices that allow sharps to be placed within a rigid disposal container, but which inhibit the later removal of sharps from the container. Many of these devices are intended primarily for use in doctors offices and hospitals where the need for such disposal containers is apparent. Since sharps are often employed in the provision of home health care, the need for an inexpensive, easy-to-use sharps disposal container for the home also exists. Some designs are also suitable for the disposal of dangerous liquids as well as sharps, but most are suitable only for the disposal of sharps because if overturned liquids would escape through their closure devices. Still other sharps disposal container designs go beyond inhibiting removal of sharps from the disposal container by providing a means by which the opening to the disposal container may be permanently sealed. However, these devices fail to include features which reduce the possibility that the container might be permanently sealed before it is full.

Consequently, a need exists for an inexpensive, easy-to-use sharps disposal container intended for use in the home as well as doctors offices and hospitals that has a closure device which permanently seals both dangerous sharps and liquids within the container and has an added feature that reduces the possibility of the container being permanently sealed before it is full.

SUMMARY OF THE INVENTION

The present invention provides a sharps disposal container cap securement arrangement designed to satisfy the aforementioned needs by avoiding the drawbacks of the prior art without introducing other drawbacks.

The present invention is directed to a sharps disposal container cap securement arrangement which comprises: (a) a container with a neck having an opening at a top thereof through which sharps may be placed for disposal within the container; (b) a cap adapted to rotatably fit, such as by screwing, down over and around the neck of the container to close the opening and preferably to provide a fluid-tight seal therewith once the cap is screwed down on the neck; (c) an annular lock collar rotatably mounted around an exterior surface of the neck of the container below the cap; (d) detent means formed on the neck of the container and on the collar for supporting the collar on the neck for undergoing movement from a lowered unlocked condition to a raised locked condition relative to the cap once the cap is screwed down on the neck of the container providing the fluid-tight seal and in response to the collar being rotated from a first to a second position relative to the neck; and (e) cooperative means formed on the collar and on the cap for locking the cap to the collar and thereby securing the cap on the neck of the container so as to prevent unscrewing and removal of the cap from the neck of the container once the cap is screwed down on the neck of the container providing the fluid-tight seal and the lock collar has been rotated from the first position to the second position relative to the neck and thereby moved from the lowered unlocked condition to the raised locked condition relative to the cap.

The neck of the container further has an external screw thread on the exterior surface of the neck below the top thereof. The cap has a continuous annular sidewall with an internal screw thread on an interior surface thereof adapted to threadably mate with the external screw thread on the exterior surface of the neck of the container.

The detent means includes features on the neck of the container and on the annular lock collar. The feature defined on the container neck is a plurality of lugs disposed in spaced relation to one another below the external screw thread on the neck of the container and attached about the exterior surface of the neck and projecting outwardly therefrom. The feature defined on the annular lock collar is pairs of spaced upper and lower recesses defined in the collar extending upwardly from a lower portion of the collar and a tapered edge leading from the upper recess of each of the pairs to the lower recess thereof. Once the collar has been rotated to a first position, the lugs are seated in the upper recesses and support the collar at a lowered unlocked condition relative to the cap. On the other hand, once the collar has been rotated to a second position, the lugs are seated in the lower recesses and support the collar at a raised locked condition relative to the cap. During rotational movement of the collar from the first position to the second position the lugs bear against the tapered edges causing the collar to also move upward from the lowered unlocked condition to the raised locked condition.

The cooperative means includes features on the annular lock collar and on the cap. The feature defined on the collar is a first row of one-way external ratchet teeth formed about an exterior surface of an upper portion of the collar. The feature defined on the cap is a second row of one-way internal ratchet teeth formed below the internal screw thread on the interior surface of the sidewall of the cap. The one-way internal ratchet teeth on the cap are complementary to the one-way external ratchet teeth on the collar and are thereby adapted to engage and interlock therewith once the cap is screwed down on the neck of the container and in response to the collar being moved relative to the cap from the lowered unlocked condition to the raised locked condition.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 2:
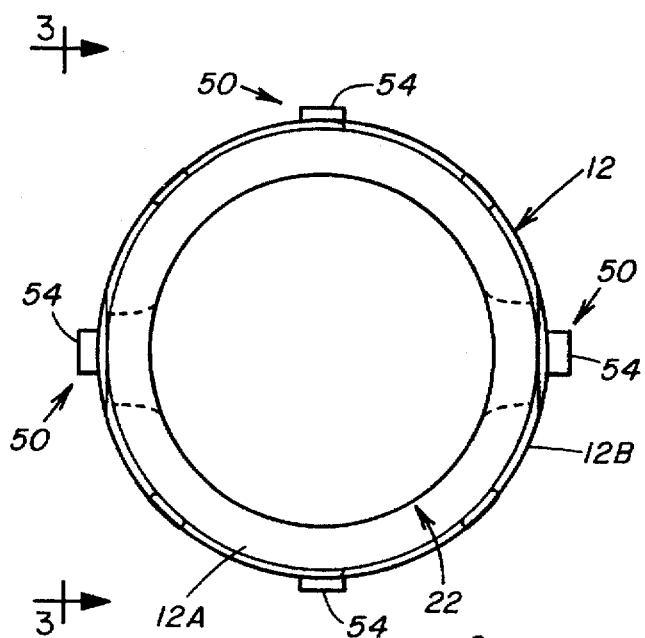
FIG. 2 is a top plan view of the neck of the sharps disposal container as seen along line 2—2 of FIG. 1.
Figure 1:
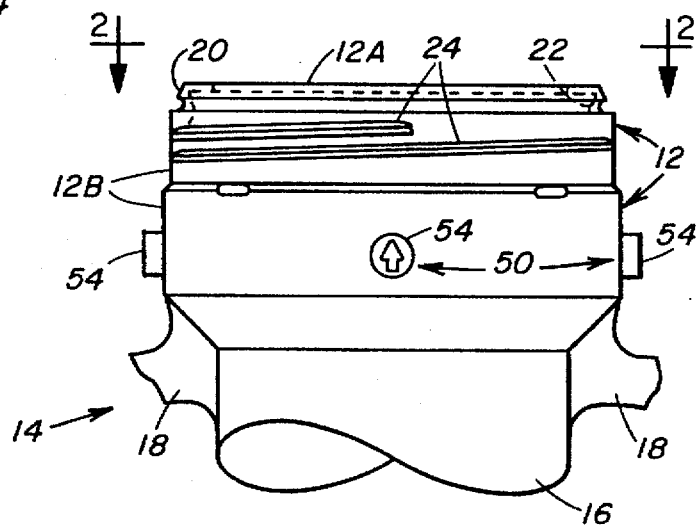
FIG. 1 is a fragmentary side elevational view of a sharps disposal container having a neck employing components of a cap securement arrangement of the present invention.
Figure 3:
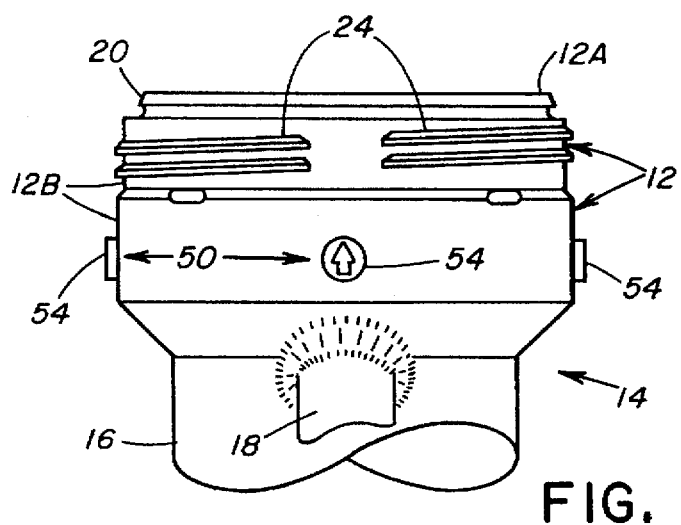
FIG. 3 is another fragmentary side elevational view of the neck of the container as seen along line 3—3 of FIG. 2.
Figure 4:
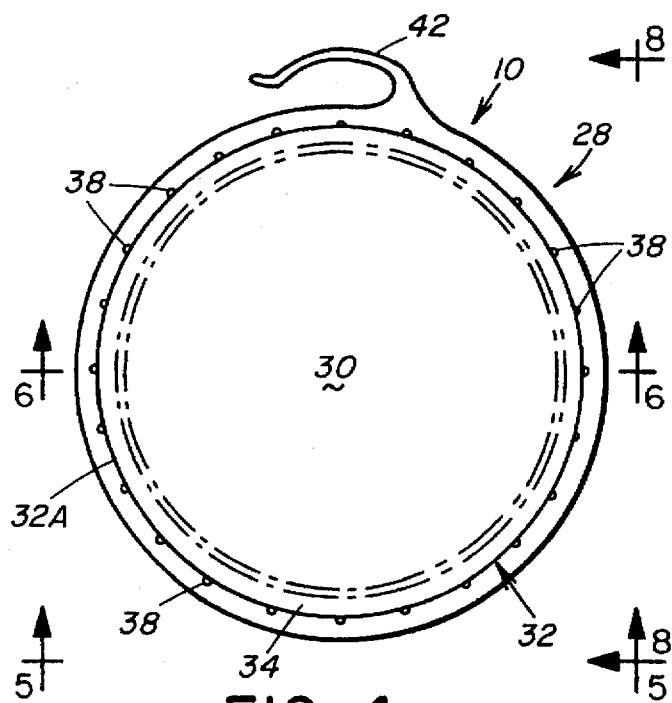
FIG. 4 is a top plan view of a cap of the arrangement for securement to the neck of the container.
Figure 7:
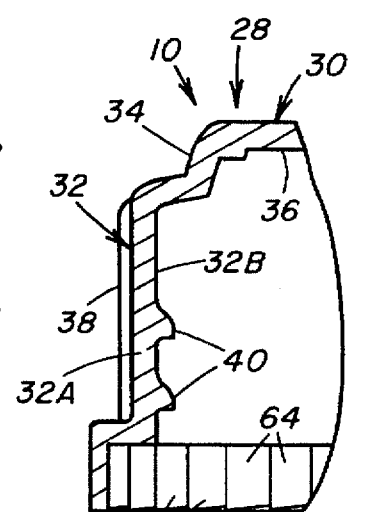
FIG. 7 is an enlarged cross-sectional view of the portion of the cap enclosed by circle 7 of FIG. 6.
Figure 6:
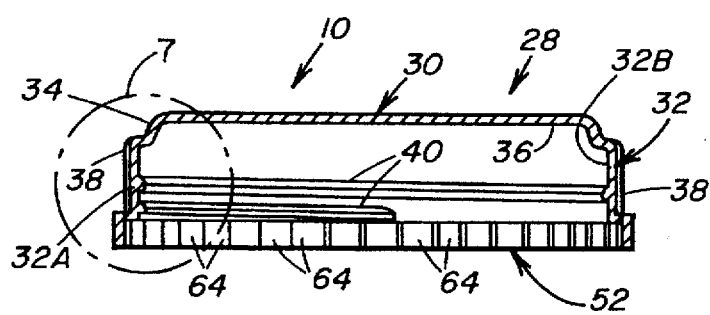
FIG. 6 is a cross-sectional view of the cap as seen along line 6—6 of FIG. 4.
Figure 8:
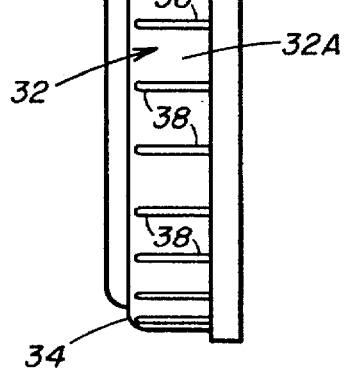
FIG. 8 is a side elevational view of the cap as seen along line 8—8 of FIG. 4.
Figure 5:
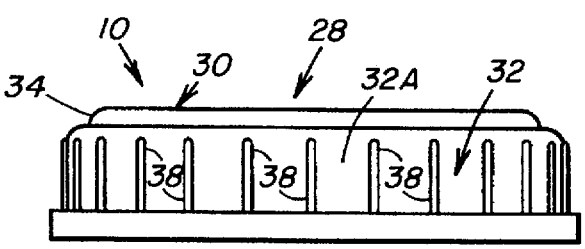
FIG. 5 is a side elevational view of the cap as seen along line 5—5 of FIG. 4.
Figure 11:
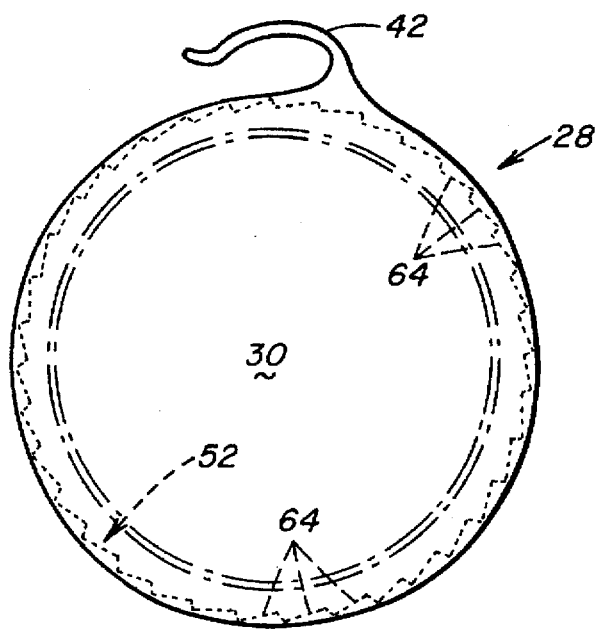
FIG. 11 is another top plan view of the cap.
Figure 9:
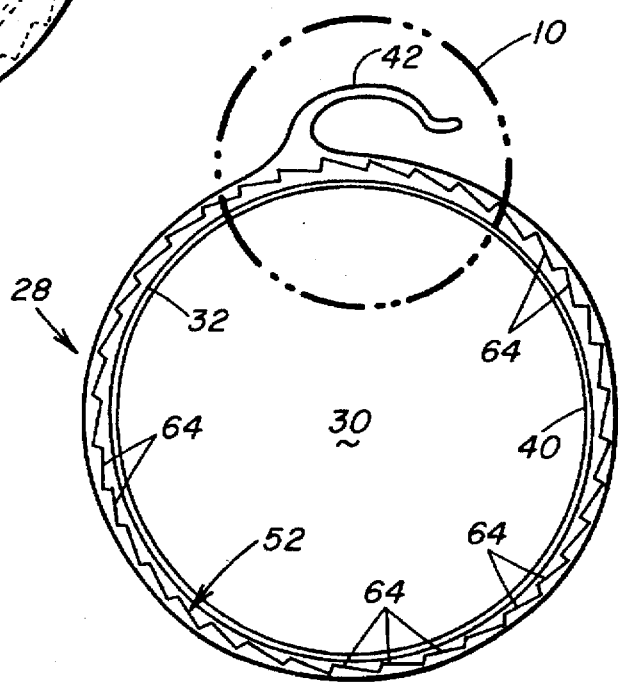
FIG. 9 is a bottom plan view of the cap.
Figure 10:
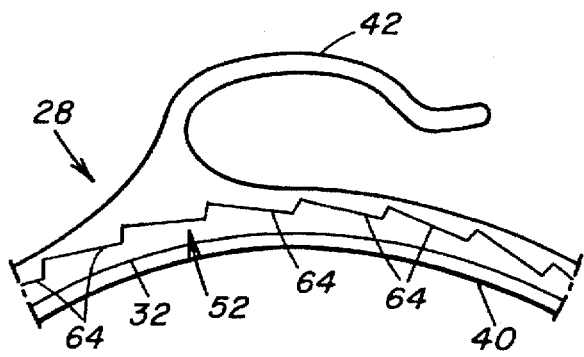
FIG. 10 is an enlarged bottom plan view of the portion of the cap enclosed by circle 10 of FIG. 9.
Figure 12:
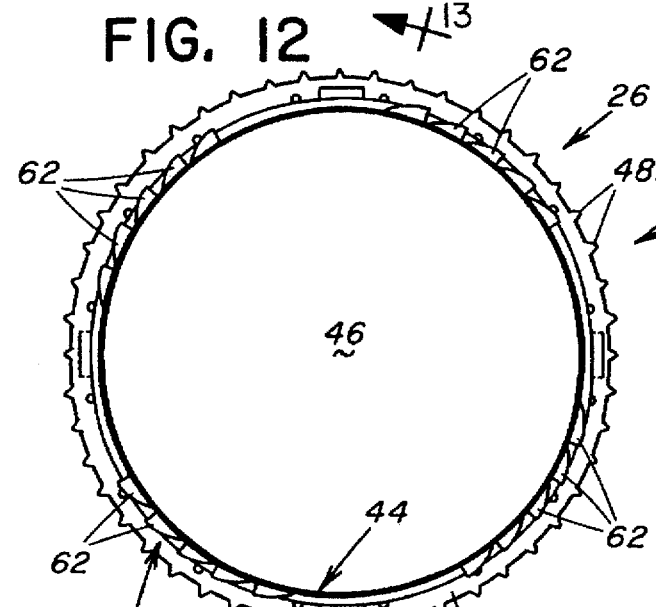
FIG. 12 is a top plan view of an annular lock collar of the arrangement for mounting about the neck of the container.
Figure 13:
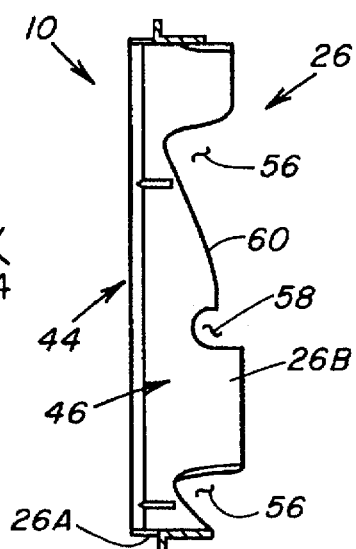
FIG. 13 is a cross-sectional view of the collar as seen along line 13—13 of FIG. 12.
Figure 14:
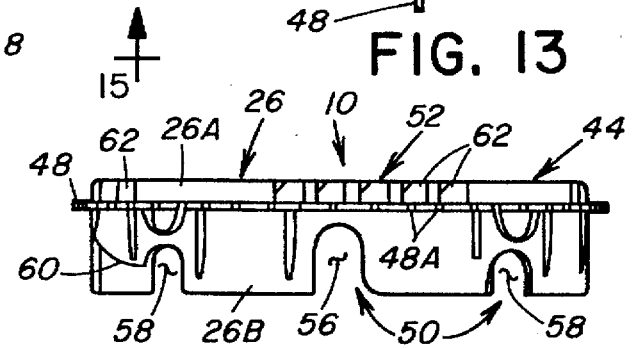
FIG. 14 is a side elevational view of the collar as seen along line 14—14 of FIG. 12.
Figure 15:
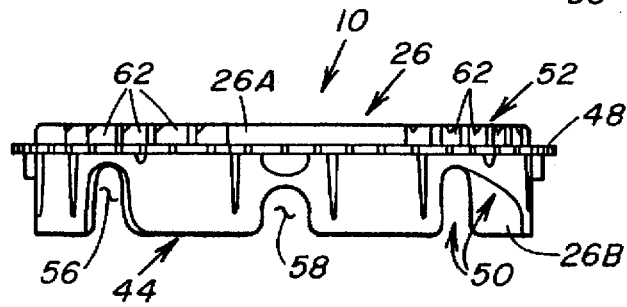
FIG. 15 is another side elevational view of the collar as seen along line 15—15 of FIG. 12.
Figure 16:
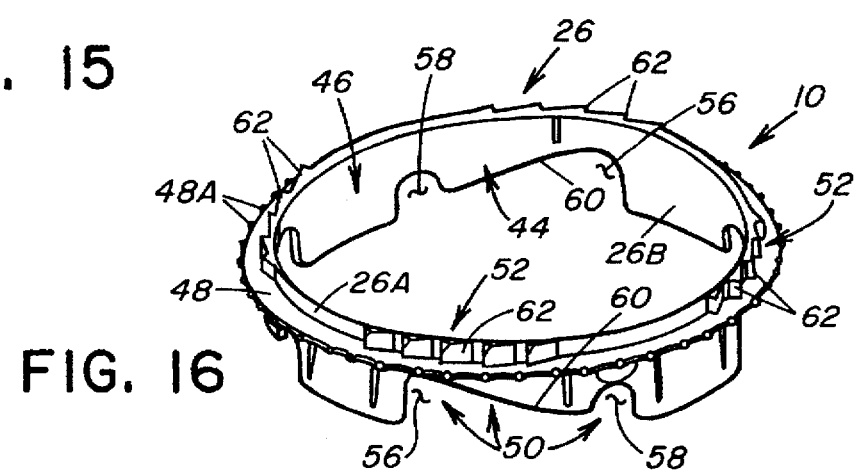
FIG. 16 is a top perspective view of the collar.

Referring to the drawings and particularly to FIGS. 1, 5, 16, 18 and 19, there is illustrated the various components of a sharps disposal container cap securement arrangement, generally designated 10, of the present invention which are employed in conjunction with a neck 12 of a sharps disposal container 14 defining an open top 12A thereon. As best seen in FIGS. 1 to 3, in addition to the neck 12, the sharps disposal container 14 typically has a hollow container body 16 (only a fragment being shown) and a pair of handles 18 (likewise only fragments being shown) which are adapted for gripping to lift and move the container 14. The neck 12 also is hollow and is attached to and extends upwardly from the top of the container body 16. The neck 12 has an exterior surface 12B and an annular rim 20 which defines an opening 22 into the container 14 at the top 12A of the neck 12 through which items such as sharps or liquids may be deposited for disposal within the container body 16. The neck 12 of the container 14 further has an external screw thread 24 formed on the exterior surface 12B of the neck 12 below the annular rim 20 and spaced above the top of the container body 16. The external screw thread 24 extends about an upper portion of the exterior surface 12B of the container neck 12.

Referring to FIGS. 4-16, the securement arrangement 10 basically includes an annular lock collar 26 adapted to rotatably mount around the neck 12 of the container 14 spaced below its top 12A, and a cap 18 adapted to screw down over the top 12A of and around the neck 12 above the lock collar 26. The lock collar 26 and cap 28 are adapted to be locked to one another such that the cap 28 is prevented from being removed from over the top 12A of the container neck 12 and provides a fluid-tight seal therewith.

The cap 28 of the arrangement 10 more particularly includes a top wall or panel 30 and a continuous annular sidewall 32 connected to and extending downwardly from a periphery 34 of the top panel 30. The top panel 30 defines a flat annular surface portion 36 adapted to overlie and engage the annular rim 20 and substantially close the opening 22 of the neck 12 of the container 14 and thereby provide the fluid-tight seal therewith when the cap 28 is screwed down on the neck 12 of the container 14. The sidewall 32 has a plurality of semicircular ridges 38 formed on an exterior surface 32A thereof for use in gripping and screwing the cap 28 onto and from the neck 12 of the container 14. An internal screw thread 40 is formed on an interior surface 32B of the sidewall 32 of the cap 28 and extends continuously thereabout and is adapted to threadably mate with the external screw thread 24 on the exterior surface 12B of the neck 12 of the container 14. The cap 28 also has a hook-shaped retainer 42 extending from and preferably integral with the exterior surface 32A of the sidewall 32 of the cap 28 for hanging the cap 18 on the container 14 after the cap 28 is removed from the neck 12 of the container 14.

The annular lock collar 26 of the arrangement 10 more particularly includes a peripheral ring 44 defining a large opening 46 therethrough. The ring 44 has a peripheral ledge 48 dividing the collar 26 into upper and lower portions 26A, 26B. The ledge 48 has a serrated edge 48A adapted for a user to grip the collar 26 to rotate it relative to the neck 12. The large opening 46 adapts the ring 44 of the collar 46 to be rotatably mounted about the neck 12 by fitting down around the exterior surface 12B thereof.

Referring now to FIGS. 1 to 19, the cap securement arrangement 10 further includes detent means 50 and cooperative locking means 52. The detent means 50 are formed on the exterior surface 12B of the neck 12 of the container 14 and on the collar 26 for supporting the collar 26 on the neck 12 to undergo movement from a lowered unlocked condition (see FIG. 18) to a raised locked condition (see FIG. 19) relative to the cap 28 once the cap 28 is screwed down on the neck 12 providing the fluid-tight seal and in response to the collar 26 being rotated from a first position (see FIG. 18) to a second position (see FIG. 19) relative to the neck 12. The cooperative locking means 52 are formed on the collar 26 and on the cap 28 for locking the cap 28 to the collar 26 and thereby securing the cap 28 on the neck 12 of the container 14 so as to prevent unscrewing and removal of the cap 28 from the neck 12 of the container 14 once the cap 28 is screwed down on the neck 12 providing the fluid-tight seal and the lock collar 26 has been rotated from the first position to the second position relative to the neck 12 and thereby moved from the lowered unlocked condition to the raised locked condition relative to the cap 28.

Referring now to FIGS. 1 to 3, 12 to 16, 18 and 19, more particularly the detent means 50 includes features on the neck 12 of the container 14 and on the annular lock collar 26. The feature defined on the container neck 12 is a plurality of dimples or lugs 54 disposed in spaced relation to one another above the container body 16 and below the external screw thread 24 on the neck 12 of the container 14. The lugs 54 are attached about the exterior surface 12B of the neck 12 and project outwardly therefrom. The features defined on the lock collar 26 include pairs of spaced upper and lower recesses 56, 58 defined in the collar 26 so as to extend upwardly from the lower portion 26B of the collar 26, and a tapered edge 60 leading from the upper recess 56 of each of the pairs thereof to the lower recess 58 thereof. On the one hand, once the collar 26 has been rotated to the first position, as shown particularly in FIG. 18, the lugs 54 are seated in the upper recesses 56 and support the collar 26 at the lowered unlocked condition. On the other hand, once the collar 26 has been rotated to the second position, as shown particularly in FIG. 19, the lugs 54 are seated in the lower recesses 58 and support the collar 26 at the raised locked condition. During rotation of the collar 26 from the first position to the second position, each lug 54 bears against one of the tapered edges 60 extending between the upper and lower recesses 56, 58 causing the collar 26 to also move upward from the lowered unlocked condition to the raised locked condition relative to the cap 28.

Referring now to FIGS. 9 to 19, the cooperative means 52 includes features on the annular lock collar 26 and on the cap 28. The feature defined on the collar 26 is a first row of one-way external ratchet teeth 62 formed about an exterior surface of the upper portion 26B of the collar 26. The feature defined on the cap 28 is a second row of one-way internal ratchet teeth 64 formed below the internal screw thread 40 on the interior surface 32B of the sidewall 32 of the cap 28. The one-way internal ratchet teeth 64 of the cap 28 are shaped complementary to the one-way external ratchet teeth 62 of the collar 26 and are thereby adapted to engage and preferably interlock therewith once the cap 28 is screwed down on the neck 12 of the container 14 to provide the fluid-tight seal and in response to the collar 26 being moved relative to the neck 12 and cap 28 from the lowered unlocked condition to the raised locked condition. Also, either the one-way external ratchet teeth 62 are continuous about the exterior surface of the upper portion 26A of the collar 26 and/or the one-way internal ratchet teeth 64 are continuous about the interior surface 32B of the sidewall 32 of the cap 28. Furthermore, either the one-way external ratchet teeth 62 or the one-way internal ratchet teeth 64 may be in a row of spaced apart groups of ratchet teeth 62 or 64 rather than in a continuous row so long as the other is in a continuous row. Finally, the one-way external ratchet teeth 62 on the collar 26 are unmeshed from and disposed below the one-way internal ratchet teeth 64 on the cap 28 when the collar 26 is disposed at the lowered unlocked condition, as shown particularly in FIG. 18. On the other hand, the one-way external ratchet teeth 62 on the collar 26 are meshed with and disposed against the one-way internal ratchet teeth 64 on the cap 28 when the collar 26 is disposed at the raised locked condition, as shown particularly in FIG. 19.

Figure 17:
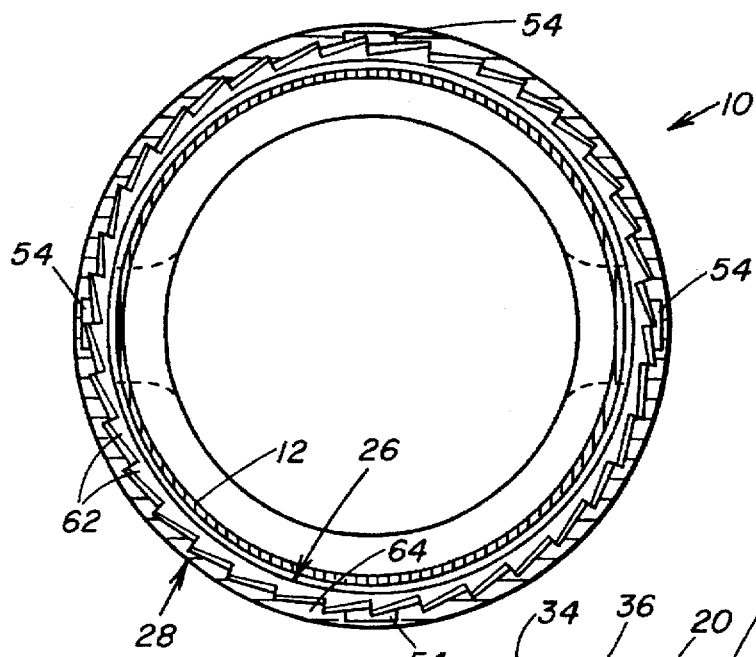
FIG. 17 is a cross-sectional view of the components of the cap securement arrangement employed on the neck of the container.
Figure 18:
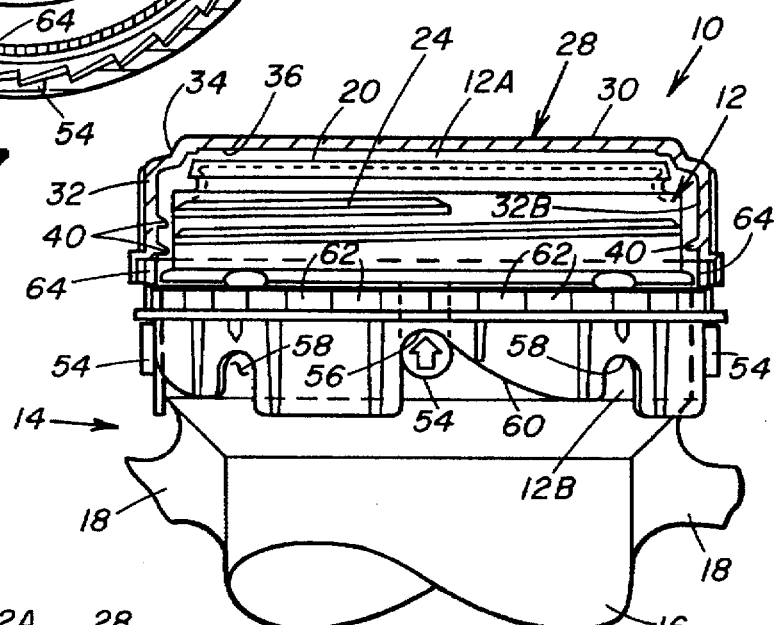
FIG. 18 is a side elevational view of the cap securement arrangement showing the cap screwed down on the neck of the container but with engagement prevented between a row of one-way ratchet teeth on the cap and a complementary row of one-way ratchet teeth on the collar by a plurality of lugs on the neck being seated in upper recesses of the collar and thereby supporting the collar at a lowered unlocked condition.
Figure 19:
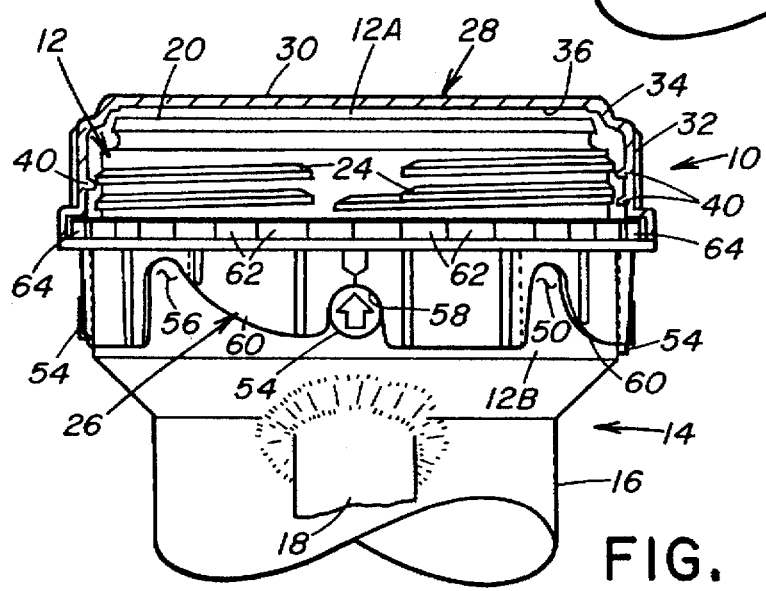
FIG. 19 is another side elevational view of the cap securement arrangement showing the cap screwed down on the neck of the container and the lugs on the neck of the container being seated in lower recesses of the collar and thereby supporting the collar at a raised locked condition such that the respective rows of oneway ratchet teeth are engaged with one another to prevent removal of the cap.

Referring now to FIGS. 17 to 19, there is shown the steps of securing the cap 28, as shown in FIGS. 4 to 11, to the annular lock collar 26, as shown in FIGS. 12 to 16, onto the neck 12 of the container 14, as shown in FIGS. 1 to 3. First, the collar 26 is fitted over the neck 12 and is moved downward until the lugs 54 on the exterior surface 12B of the neck 12 are seated in the upper recesses 56 of the lower portion 26B of the collar 26. With the lugs 54 in this first position, the collar 26 is in the lower unlocked condition. Next, the cap 28 is placed over the top 12A of the neck 12 and screwed down around the neck 12 of the container The cap 28 and the collar 26 cannot be secured to one another with the collar 26 in the lower unlocked condition, as shown particularly in FIG. 18. The collar 26 is then rotated so that the lugs 54 of the neck 12 are seated in the lower recesses 58 of the lower portion 26B of the collar 26. With the lugs 54 in this second position, the collar 26 is now in the raised locked condition where the one-way external ratchet teeth 62 on the exterior surface of the upper portion 26A of the collar 26 engage with the one-way internal ratchet teeth 64 on the interior surface 32B of the sidewall 32 of the cap 28 once it has been screwed down on the neck 12 of the container 14. This engagement of the one-way external and internal ratchet teeth 62, 64 secures the cap 28 to the collar 26 and thereby onto the neck 12 of the container 14 such that the cap 28 cannot readily be unscrewed therefrom, as shown particularly in FIG. 19.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

I claim:

1. A sharps disposal container cap securement arrangement, comprising:

(a) a container with a neck having an opening at a top thereof through which sharps may be placed for disposal within said container and a plurality of lugs disposed in spaced relation to one another about and attached to and projecting outwardly from an exterior surface of said neck and spaced below said top thereof;

(b) a cap adapted to rotatably fit downward over and around said neck of said container above said lugs thereon so as to close said opening through said neck of said container;

(c) an annular lock collar open at opposite axially spaced upper and lower portions and rotatably mounted around said neck of said container spaced below said top thereof and below said cap, said lock collar having pairs of spaced upper and lower recesses defined therein extending upwardly from said lower portion of said collar and a tapered edge leading from said upper recess of each of said pairs to said lower recess thereof, said lugs of said neck of said container being seated in said upper recesses and supporting said collar at a lowered unlocked condition relative to said cap once said collar has been rotated to a first position, said lugs of said neck of said container being seated in said lower recesses and supporting said collar at a raised locked condition relative to said cap once said collar has been rotated to a second position, each of said lugs bearing against one of said tapered edges extending between said upper and lower recesses during rotation of said collar to move said collar from said lowered unlocked condition upwardly to said raised locked condition; and (d) cooperative means formed on said collar and on said cap for locking said cap to said collar and thereby securing said cap on said neck of said container so as to prevent removal of said cap from said neck of said container once said cap is fitted down on said neck of said container and said collar has been rotated from said first position to said second position relative to said neck and thereby moved from said lowered unlocked condition to said raised locked condition relative to said cap.

2. The arrangement of claim 1 wherein said cooperative means are complementary first and second rows of one-way ratchet teeth respectively formed on said collar and on said cap, said first and second rows of one-way ratchet teeth being adapted to engage each other when said cap is fitted downward on said neck of said container and said collar rotated from said first position to said second position relative to said neck to thereby prevent removal of said cap from said neck of said container.

3. The arrangement of claim 1 wherein said cap has a top panel and a continuous annular sidewall connected to and extending downwardly from a periphery of said top panel.

4. The arrangement of claim 3 wherein said neck of said container has an annular rim at said top of said neck defining said opening thereto.

5. The arrangement of claim 4 wherein said top panel defines a flat annular surface portion adapted to overlie and engage said annular rim and thereby substantially close said opening of said neck of said container and to provide a fluid-tight seal therewith when said cap is fitted down on said neck of said container.

6. The arrangement of claim 3 further comprising:
   (e) a continuous external screw thread attached on and extending about said exterior surface of said neck of said container between said top thereof and said dimples thereon; and
   (f) a continuous internal screw thread formed on an interior surface of said sidewall of said cap and adapted to threadably mate with said external screw thread on said exterior surface of said neck of said container.

7. The arrangement of claim 3 wherein said cooperative means includes:
   a first row of one-way external ratchet teeth formed about an exterior surface of said upper portion of said collar; and
   a second row of one-way internal ratchet teeth formed on an interior surface of said sidewall of said cap, said second row of one-way internal ratchet teeth being complementary to said first row of one-way external ratchet teeth when said cap is fitted down on said neck of said container.

8. The arrangement of claim 7 wherein said one-way external ratchet teeth are arranged in spaced apart groups about said exterior surface of said upper portion of said collar.

9. The arrangement of claim 7 wherein said one-way internal ratchet teeth are continuous about said interior surface of said sidewall of said cap.

10. The arrangement of claim 7 wherein said one-way external ratchet teeth on said collar are unmeshed from and disposed below said one-way internal ratchet teeth on said cap when said collar is disposed at said lowered unlocked condition relative to said cap, said one-way external ratchet teeth on said collar being meshed with and disposed against said one-way internal ratchet teeth on said cap when said collar is disposed at said raised locked condition relative to said cap.

11. The arrangement of claim 1 wherein said cap has a hook-shaped retainer extending from a side of said cap for securing and retaining said cap on said container when said cap is completely removed from said neck of said container.

12. A sharps disposal container cap securement arrangement, comprising:
   (a) a container with a neck having an opening at a top thereof through which sharps may be placed for disposal within said container;
   (b) a cap adapted to rotatably fit down over and around said neck of said container so as to close said opening through said neck of said container, said cap having a row of one-way ratchet teeth formed thereon;
   (c) an annular lock collar rotatably mounted around said neck of said container below said cap and having a second row of one-way ratchet teeth formed thereon being complementary to said first row of one-way ratchet teeth on said cap, said first and second rows of one-way ratchet teeth being adapted to engage each other to thereby prevent removal of said cap from said neck of said container in response to rotatable movement of said lock collar from a first position to a second position relative to said neck once said cap is fitted down on said neck of said container; and
   (d) detent means formed on said neck of said container and on said collar for supporting said collar on said neck to undergo rotational movement from said first position to said second position relative to said neck and thereby cause said collar to also move from a lowered unlocked condition relative to said cap in which said first and second rows of one-way ratchet teeth are disengaged from one another to a raised locked condition relative to said cap in which said first and second rows of one-way ratchet teeth are engaged with one another.

13. The arrangement of claim 12 wherein said detent means includes:
   a plurality of lugs disposed in spaced relation to one another about and attached to and projecting outwardly from an exterior surface of said neck and spaced below said top thereof;
   pairs of spaced upper and lower recesses defined in said collar extending upward from a lower portion thereof; and
   a tapered edge leading from said upper recess of each of said pairs to said lower recess thereof, said lugs of said neck of said container being seated in said upper recesses and supporting said collar at said lowered unlocked condition once said collar has been rotated to said first position, said lugs of said neck of said container being seated in said lower recesses and supporting said collar at said raised locked condition once said collar has been rotated to said second position, each of said lugs bearing against one of said tapered edges extending between said upper and lower recesses during rotation of said collar to cause movement of said collar from said lowered unlocked condition upwardly to said raised locked condition.

14. The arrangement of claim 12 wherein said cap has a top panel and a continuous annular sidewall connected to and extending downwardly from a periphery of said top panel.

15. The arrangement of claim 14 wherein said neck of said container has an annular rim at said top of said neck defining said opening thereto.

16. The arrangement of claim 15 wherein said top panel defines a flat annular surface portion adapted to overlie and engage said annular rim and thereby close said opening of said neck of said container and to provide a fluid-tight seal therewith when said cap is fitted down on said neck of said container.

17. The arrangement of claim 14 further comprising:
(e) a continuous external screw thread attached on and extending about an exterior surface of said neck of said container; and
(f) a continuous internal screw thread formed on an interior surface of said sidewall of said cap and adapted to threadably mate with said external screw thread on said exterior surface of said neck of said container.

18. The arrangement of claim 14 wherein said first row of one-way ratchet teeth of said collar are formed about an exterior surface of an upper portion of said collar and said second row of one-way ratchet teeth of said cap are formed on an interior surface of said sidewall of said cap.

19. The arrangement of claim 18 wherein said one-way external ratchet teeth are arranged in spaced apart groups about said exterior surface of said upper portion of said collar.

20. The arrangement of claim 18 wherein said one-way internal ratchet teeth are continuous about said interior surface of said sidewall of said cap.

21. The arrangement of claim 18 wherein said one-way external ratchet teeth on said collar are unmeshed from and disposed below said one-way internal ratchet teeth on said cap when said collar is disposed at said lowered unlocked condition relative to said cap, said one-way external ratchet teeth on said collar being meshed with and disposed against said one-way internal ratchet teeth on said cap when said collar is disposed at said raised locked condition relative to said cap.

22. The arrangement of claim 12 wherein said cap has a hook-shaped retainer extending from a side of said cap for securing and retaining said cap on said container when said cap is completely removed from said neck of said container.

23. A sharps disposal container cap securement arrangement, comprising:
(a) a container with a neck having an opening at a top thereof through which sharps may be placed for disposal within said container;
(b) a cap adapted to rotatably fit downward over and around said neck of said container to close said opening and to provide a fluid-tight seal therewith when said cap is fitted down on said neck;
(c) an annular lock collar rotatably mounted around an exterior surface of said neck of said container below said cap;
(d) detent means formed on said neck of said container spaced below said top thereof and on said collar for supporting said collar on said neck for movement from a lowered unlocked condition to a raised locked condition relative to said cap once said cap is fitted down on said neck of said container providing said fluid-tight seal and in response to said collar being rotated from a first position to a second position relative to said neck; and
(e) cooperative means formed on said collar and on said cap for locking said cap to said collar and thereby securing said cap on said neck of said container so as to prevent removal of said cap from said neck of said container once said cap is fitted down on said neck of said container providing said fluid-tight seal and in response to said collar being rotated from said first position to said second position relative to said neck and thereby moved from said lowered unlocked condition to said raised locked condition relative to said cap.

24. The arrangement of claim 23 further comprising:
(f) a continuous external screw thread attached on and extending about said exterior surface of said neck of said container between said top thereof and said detent means thereon; and
(g) a continuous internal screw thread formed on an interior surface of a sidewall of said cap and adapted to threadably mate with said external screw thread on said exterior surface of said neck of said container.

25. The arrangement of claim 23 wherein said cooperative means includes:
a first row of one-way external ratchet teeth formed about an exterior surface of an upper portion of said collar; and
a second row of one-way internal ratchet teeth formed on an interior surface of a sidewall of said cap, said second row of one-way internal ratchet teeth being complementary to said first row of one-way external ratchet teeth and engaged with said first row of one-way ratchet teeth once said cap is fitted down on said neck of said container and in response to said collar being rotated from said first position to said second position relative to said neck.

26. The arrangement of claim 25, wherein said one-way external ratchet teeth are arranged in spaced apart groups about said exterior surface of said upper portion of said collar.

27. The arrangement of claim 25 wherein said one-way internal ratchet teeth are continuous about said interior surface of said sidewall of said cap.

28. The arrangement of claim 25 wherein said one-way external ratchet teeth on said collar are unmeshed from and disposed below said one-way internal ratchet teeth on said cap when said collar is disposed at said lowered unlocked condition relative to said cap, said one-way external ratchet teeth on said collar being meshed with and disposed against said one-way internal ratchet teeth on said cap when said collar is disposed at said raised locked condition relative to said cap.

29. The arrangement of claim 23 wherein said detent means includes a plurality of lugs disposed in spaced relation to one another about and attached to and projecting outwardly from said exterior surface of said neck and spaced below said top thereof.

30. The arrangement of claim 29 wherein said detent means further includes:
pairs of spaced upper and lower recesses defined in said collar extending upward from a lower portion thereof; and
a tapered edge leading from said upper recess of each of said pairs to said lower recess thereof, said lugs of said neck of said container being seated in said upper recesses and supporting said collar at said lowered unlocked condition once said collar has been rotated to said first position, said lugs of said neck of said container being seated in said lower recesses and supporting said collar at said raised locked condition once said collar has been rotated to said second position, each of said lugs bearing against one of said tapered edges extending between said upper and lower recesses during rotation of said collar to cause movement of said collar from said lowered unlocked condition upwardly to said raised locked condition.

* * * * *